United States Patent
Le Neel et al.

(10) Patent No.: US 9,435,763 B2
(45) Date of Patent: Sep. 6, 2016

(54) ABSOLUTE TEMPERATURE METHOD FOR DISPOSABLE GLUCOSE STRIP

(71) Applicant: STMicroelectronics Pte Ltd., Singapore (SG)

(72) Inventors: Olivier Le Neel, Singapore (SG); Suman Cherian, Singapore (SG)

(73) Assignee: STMICROELECTRONICS PTE LTD., Singapore (SG)

( * ) Notice: Subject to any disclaimer, the term of this patent is extended or adjusted under 35 U.S.C. 154(b) by 519 days.

(21) Appl. No.: 13/929,515

(22) Filed: Jun. 27, 2013

(65) Prior Publication Data

US 2015/0001071 A1 Jan. 1, 2015

(51) Int. Cl.
*G01N 27/327* (2006.01)

(52) U.S. Cl.
CPC ........ *G01N 27/3274* (2013.01); *G01N 27/327* (2013.01)

(58) Field of Classification Search
CPC ..................... G01N 27/3271; G01N 27/3272; G01N 27/3274
See application file for complete search history.

(56) References Cited

U.S. PATENT DOCUMENTS

| 5,391,250 | A | 2/1995 | Cheney, II et al. |
| 8,617,381 | B2 * | 12/2013 | Sun .......................... A61B 5/01 204/400 |
| 2009/0000947 | A1 * | 1/2009 | Akahori ............ G01N 27/3272 204/403.14 |
| 2012/0165635 | A1 | 6/2012 | Radhakrishnan et al. |
| 2012/0168882 | A1 | 7/2012 | Cherian et al. |
| 2013/0010826 | A1 | 1/2013 | Le Neel et al. |
| 2013/0168815 | A1 | 7/2013 | Le Neel et al. |
| 2015/0001075 | A1 | 1/2015 | Le Neel et al. |

OTHER PUBLICATIONS

Zhu et al., "Planar Amperometric Glucose Sensor Based on Glucose Oxidase Immobilized by Chitosan Film on Prussian Blue Layer." ISSN 1424-8220, Sensors 2002, 2, pp. 127-136 (10 pages).

* cited by examiner

*Primary Examiner* — Alexander Noguerola
(74) *Attorney, Agent, or Firm* — Seed IP Law Group PLLC (57) ABSTRACT

A bio-fluid test strip includes a fluid receiving area and a contact pad area for interfacing with a fluid sensing device. The test strip includes a fluid sensing electrodes and a first temperature sensing resistor in the fluid receiving area. The test strip further includes a second temperature sensing resistor in the contact pad area. The first and second temperature sensing resistors together provide an indication of the temperature difference between the fluid sensing area and ambience.

21 Claims, 13 Drawing Sheets

ABSOLUTE TEMPERATURE METHOD FOR DISPOSABLE GLUCOSE STRIP

BACKGROUND

1. Technical Field

The present disclosure relates to the field of fluid sensors. The present disclosure relates more particularly to the field of disposable biosensor test strips.

2. Description of the Related Art

Biosensors are devices that utilize biological reactions to identify analyte species such as glucose, proteins, hormones, nucleotides etc. Some biosensors are designed to output a current indicative of the presence of the analyte to be detected. As the size of the biosensors scales downward in order to reduce costs of manufacturing biosensors, the dimensions of the sensing area also decrease. Due to this, the measured current signal due to electrochemical reactions is also decrease to the range of nano-amperes (nA) or even pico-amperes (pA).

Highly sensitive measurements are needed to obtain accurate and reproducible signals especially for the detection of low and ultralow concentrations of species such as C-reactive proteins. For highly sensitive, high-performance biosensors, the measuring conditions need to be carefully monitored to ensure accuracy measurements.

BRIEF SUMMARY

One embodiment is a fluid test strip for testing the presence or concentration of a particular analyte within a fluid. The fluid test strip includes a substrate and a dielectric material on the substrate. Sensing electrodes are positioned on the dielectric material in a fluid receiving area. Contact pads are also positioned on the dielectric material. Conductive signal traces connect the detection electrodes to respective contact pads. A reactive enzyme is positioned on the dielectric material and on the sensing electrodes in the fluid receiving area. The fluid test strip includes a differential temperature sensor. The differential temperature sensor includes a first and a second temperature sensing element. The first temperature sensing element is positioned in the fluid receiving area. The second temperature sensing element is positioned adjacent to the contact pads. Together the first and the second temperature sensing elements provide an indication of the temperature difference between the fluid and the ambient environment.

The fluid test strip is configured to be coupled to a fluid test strip reader. The fluid test strip reader applies respective voltages to the electrodes via the contact pads. When the fluid to be tested is placed in the fluid receiving area of the test strip, a chemical reaction occurs between the enzyme and the fluid. The strength of the chemical reaction is dependent upon concentration of the analyte in the fluid. A current passes between the electrodes through the reactive enzyme. The magnitude of the current corresponds to the strength of the chemical reaction. The fluid test strip reader measures this current to provide an indication of the concentration of the analyte in the fluid. The fluid test strip reader also supplies voltages to the differential temperature sensor and obtains an indication of the temperature difference between the fluid and the ambience. The fluid test strip reader includes an absolute temperature sensor configured to measure the ambient temperature. The fluid test strip reader can calculate the temperature of the fluid using the absolute ambient temperature and the temperature difference data.

The fluid test strip reader measures the concentration of the analyte based on the current in the temperature sensing element and the current between the electrodes. Because the reaction rate between the enzyme and the analyte is also temperature dependent, obtaining a measurement of the temperature of the fluid leads to a more accurate measurement of the concentration of the analyte in the fluid.

DETAILED DESCRIPTION

Figure 1:
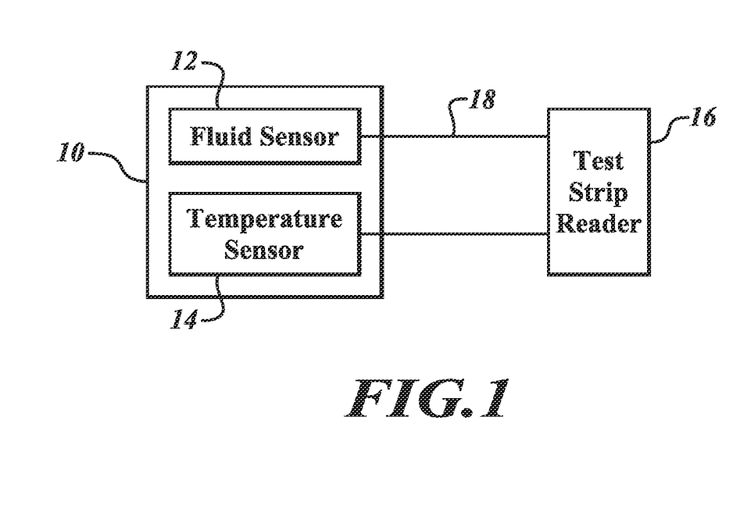
FIG. 1 is a block diagram of a fluid test strip and a fluid test strip reading device according to one embodiment.

FIG. 1 is a block diagram of a fluid sensing system including a fluid test strip 10 communicatively coupled to a fluid test strip reader 16. The fluid test strip 10 includes a fluid sensor 12, a temperature sensor 14, and communication lines 18 for electrically connecting with the fluid test strip reader 16.

The fluid test strip 10 and fluid test strip reader 16 are configured to measure the concentration or merely detect the presence of an analyte in a fluid that is placed on the fluid sensor 12 of the fluid test strip 10. The fluid test strip 10 and the fluid test strip reader 16 function by coupling the fluid test strip 10 to the fluid test strip reader 16 and by placing a small amount of test fluid on the fluid sensor 12 of the fluid test strip 10. The fluid test strip reader 16 supplies a voltage to the fluid sensor 12 and via the communication lines 18. The fluid sensor 12 passes a sensor signal back to the fluid test strip reader 16 indicative of the concentration of the analyte in the fluid.

In some instances the magnitude of the sensor signal can be affected by both the concentration of the analyte and the temperature of the fluid. For this reason the fluid test strip 10 includes the temperature sensor 14. The temperature sensor 14 provides a temperature signal indicative of the temperature of the fluid. The fluid test strip reader 16 outputs a measurement of the concentration of the analyte in the fluid based on both the sensor signal and the temperature signal. In this way, the fluid test strip reader 16 can output an accurate measurement of the concentration of the analyte in the fluid by taking into consideration the temperature of the fluid.

In one embodiment, the temperature sensor 14 is a differential temperature sensor providing a signal that indicates the difference in temperature between the test fluid and the ambience. The temperature sensor 14 includes a first temperature sensor element positioned in a fluid receiving area of the fluid test strip 10 and a second temperature sensor element at a position on the fluid test strip 10 thermally isolated from the fluid receiving area. Together, the first and second temperature sensor elements provide the differential temperature signal indicative of the difference in temperature between the test fluid and the ambience.

It is desirable that the fluid test strip 10 be relatively inexpensive to manufacture, for this reason the temperature sensor 14 of the fluid test strip 10 may not include circuitry that calculates and outputs the fluid temperature from the temperature signal. Instead the circuitry can be located in the fluid test strip reader 16. The fluid test strip reader 16 can include a separate temperature sensor that measures the absolute temperature of the ambience. The fluid test strip reader 16 also receives the differential temperature signal from the fluid test strip 10. Because the differential temperature signal indicates the difference in temperature between the ambience and the fluid, the fluid test strip reader 16 can calculate the absolute temperature of the fluid based on the differential temperature signal and the absolute temperature of the ambience.

In one example, the fluid test strip 10 is a blood glucose test strip. The blood glucose test strip measures the concentration of glucose in a patient's blood. By placing the blood glucose test strip into the test strip reader 16, and by placing a small amount of the patient's blood on the test strip, the test strip reader 16 can provide a measurement of the concentration of glucose in the patient's blood.

The blood glucose test strip includes a fluid receiving area on which the small amount of the patient's blood is placed for testing. The fluid sensor 12 comprises electrodes located in the fluid receiving area of the fluid test strip 10. The blood glucose test strip includes a reactive enzyme, such as glucose oxidase, on the electrodes in the fluid receiving area. When blood is placed on the reactive enzyme in the fluid receiving area, the enzyme reacts with the glucose in the blood causing current to flow between the electrodes. The reaction between the enzyme the glucose becomes stronger as the concentration of glucose increases. The current flowing between the electrodes increases as the reaction become stronger. The magnitude of the current flowing between the electrodes is indicative of the concentration of glucose in the blood.

However, the strength of the reaction between the glucose and the enzyme is also dependent on temperature. For a given concentration of glucose in the patient's blood, the reaction between the enzyme in the glucose is different for different temperatures. Even if the temperature of the blood changes by a very small amount, the measurement of glucose in the blood can be affected significantly. Having an accurate measurement of the temperature of the fluid can help ensure an accurate measurement of the concentration of glucose in the blood.

In one example, the temperature sensor 14 includes a first temperature sensing resistor positioned in the fluid receiving area of the test strip 10 and a second temperature sensing resistor positioned in a portion of the test strip thermally separated from the fluid receiving area. The temperature sensing resistors are formed of a material having a constant temperature coefficient of resistance (TCR) over the range of likely fluid temperatures. In other words the resistance of the temperature sensing resistors changes linearly with changes in temperature over a range of probable temperatures of the fluid. In the case of a blood glucose test strip, the temperature of the fluid is likely to be within a few degrees of 37° C., the normal body temperature of a healthy individual. Thus, for a blood glucose sensor, it is beneficial for the temperature coefficient of resistance of the first temperature sensing resistor to be constant for a small range of temperatures around 37° C. The TCR of the second temperature sensing resistor should be constant in the likely range of room temperatures, for example between 15° C. and 30° C. For other types of fluid test strips 10, the range of possible temperatures may be much larger.

In one example both the first and second temperature sensing resistors are made of platinum. Platinum has a relatively constant TCR of about 3850 ppm/° C. over a wide range of temperatures. The resistance of the platinum temperature sensing resistors provides a reliable indication of the difference in temperature between the fluid and the ambience. This indication of the temperature difference between the fluid and ambience can in turn be used to calculate an accurate value of the temperature of the fluid and the concentration of the analyte in the fluid.

While a blood glucose sensor has been described as one example of a fluid test strip 10, many other embodiments are possible. For example, the fluid test strip 10 can be a protein sensor, a hormone sensor, a nucleotide sensor, or large number of other types of sensors.

Figure 2:
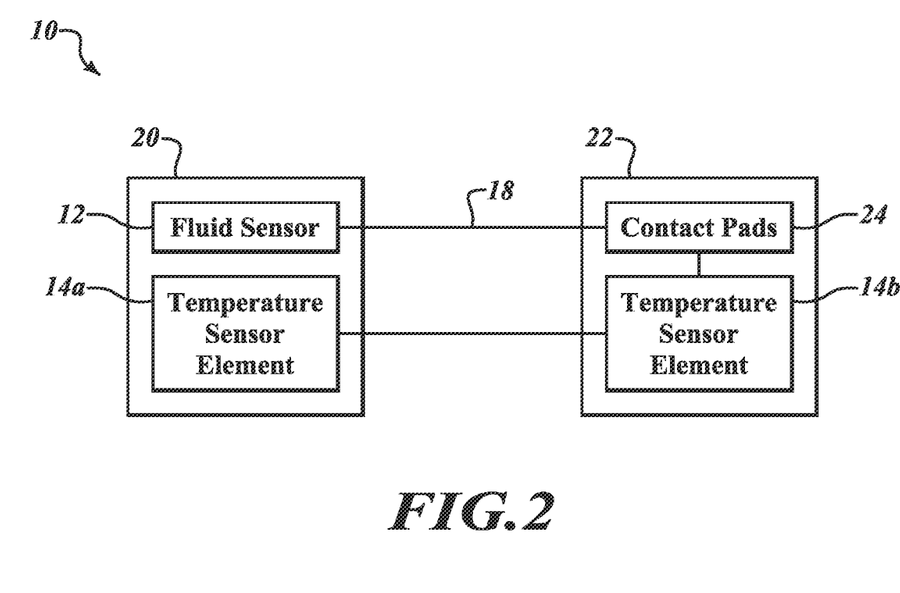
FIG. 2 is a block diagram of the fluid test strip.

FIG. 2 is a block diagram of a fluid test strip 10 according to one embodiment. The fluid test strip 10 includes a fluid receiving area 20 and a contact pads area 22. Signal lines 18 are positioned between the fluid receiving area 20 and the contact pads area 22.

The fluid receiving area 20 includes a fluid sensor 12 and a first temperature sensor element 14a. The contact pad area 22 includes contact pads 24 and the second temperature sensor element 14b. Signal lines 18 connect the fluid sensor 12 to contact pads 24. Signal lines 18 also connect the first and second temperature sensor elements 14a and 14b to the contact pads 24.

When the fluid test strip 10 is in use, it is coupled to a fluid test strip reader 16 and a small amount the fluid is placed in the fluid receiving area 20. The test strip reader 16 applies voltages to the contact pads 24. The fluid sensor 12 returns a sensor signal to the test strip reader 16 the via the contact pads 24. The sensor signal is indicative of the concentration of the analyte in the fluid. The temperature sensor elements 14a and 14b return a differential temperature signal to the test strip reader 16 via the contact pads 24. The test strip reader 16 calculates the concentration of the analyte based on the differential temperature signal and the sensor signal.

The first temperature sensor element 14a is thermally coupled to the fluid placed in the fluid receiving area 20 such that the temperature sensor element 14a is at the same temperature as the fluid. The second temperature sensor element 14b is positioned sufficiently far from the fluid receiving area 20 that the second temperature sensor element 14b is thermally isolated from the fluid. The second temperature sensor element 14b is therefore at the same temperature as the ambience. More particularly, the second temperature sensor element 14b is at the same temperature as the test strip reader 16.

In one embodiment, the test strip reader 16 includes a separate temperature sensor which measures the absolute temperature of the ambience. The test strip reader 16 then calculates the temperature of the fluid based on the absolute temperature of the ambience and the differential temperature signal. Because the second temperature sensor element 14b is at the same temperature as the test strip reader 16, the differential temperature signal is an accurate value of the temperature difference between the fluid and the test strip reader 16.

Because the strength of the reaction between the analyte and an enzyme placed on the fluid receiving area 20 is partially dependent on the temperature of the fluid, the test strip reader 16 take into account the temperature of the fluid when calculating the concentration of the analyte. The test strip reader 16 calculates the concentration of the analyte based on the temperature signal and the absolute temperature of the fluid.

Figure 3:
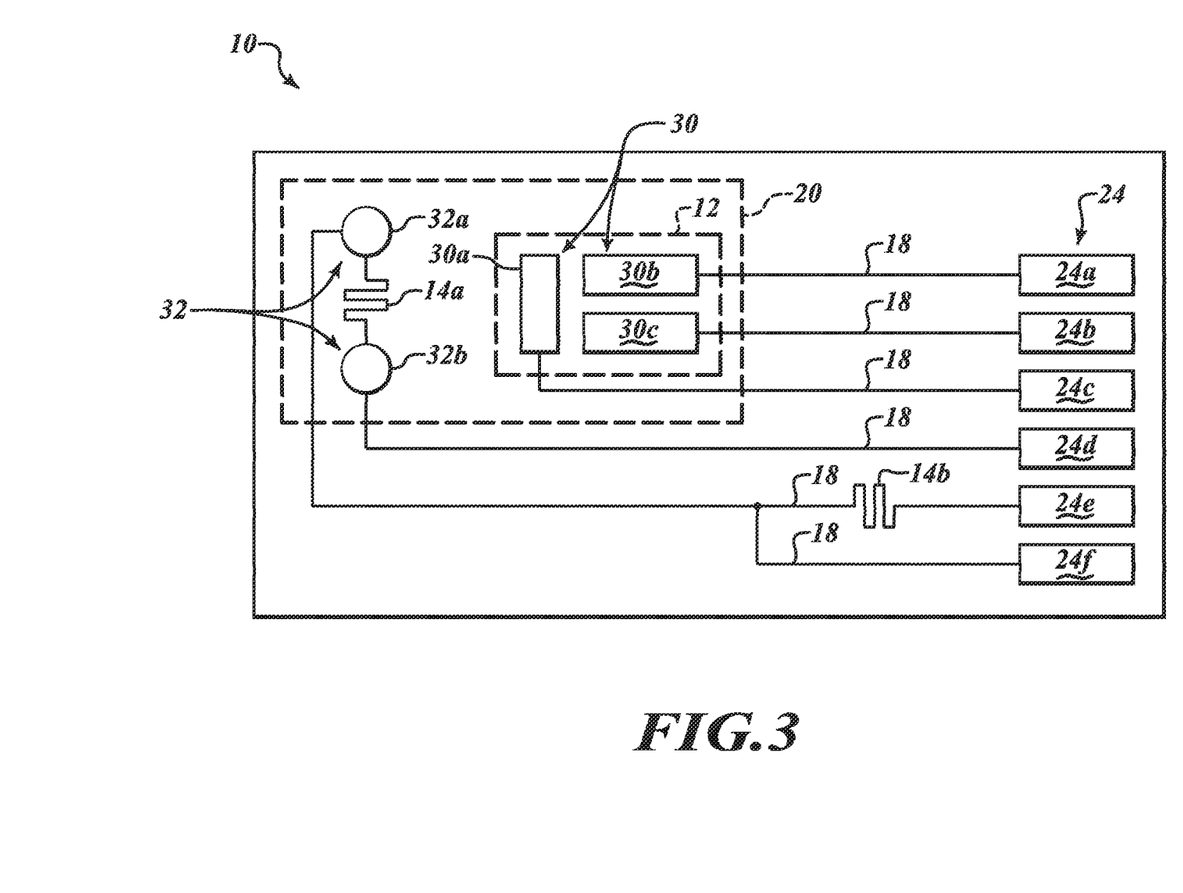
FIG. 3 is a top view of a fluid test strip according to one embodiment.

FIG. 3 is a simplified schematic of a fluid test strip 10 according to one embodiment. The fluid test strip 10 includes a fluid receiving area 20. Sensor electrodes 30, labeled here individually as 30*a*, 30*b*, and 30*c*, are positioned in the fluid receiving area 20. A first temperature sensor element 14*a* is positioned in the fluid receiving area 20. Thermal connectors 32, labeled here individually as 32*a* and 32*b*, are also positioned in the fluid receiving area 20 and are electrically coupled on opposing ends of the first temperature sensor element 14*a*. A second temperature sensor element 14*b* is positioned adjacent to the contact pad 24*e*. Contact pads 24, here labeled individually as 24*a*-24*f* are connected by signal lines 18 to the sensing electrodes 30*a*, 30*b*, 30*c* and the first and second temperature sensor elements 14*a*, 14*b*.

The fluid test strip 10 is configured to output at the contact pads 24*a*-24*f* an indication of both the concentration of an analyte in the fluid and the temperature difference between the fluid and the ambience. This is accomplished by placing the fluid test strip 10 in a fluid test strip reader 16 as described with relation to FIG. 1, and placing a small amount of the fluid on the fluid receiving area 20. The fluid test strip reader 16 applies test voltages to the contact pads 24*a*-24*f* and reads signals from the contact pads 24*a*-24*f* and computes a value of the concentration of the analyte in the fluid.

In one example, the fluid test strip reader 16 obtains an indication of the concentration of the analyte from the fluid test strip 10 by applying a voltage, for example 5 V, between contact pads 24*a* and 24*b*. The analyte in the fluid reacts with an enzyme covering the fluid receiving area. The reaction between the analyte and the enzyme enables a sensor current to flow between electrodes 30*b* and 30*c*. The magnitude of the sensor current depends on the strength of the reaction between the enzyme in the analyte. The strength of the reaction between the enzyme in the analyte depends on the concentration of the analyte in the fluid. The sensor current therefore provides an indication of the concentration of the analyte in the fluid.

The fluid test strip reader 16 obtains an indication of the temperature difference between the fluid and the ambience by applying a voltage, for example 5 V, between contact pads 24*d* and 24*e* and by measuring the voltage at the contact pad 24*f*. The voltage applied across the contact pads 24*d* and 24*e* causes a temperature current to flow through the temperature sensor elements 14*a* and 14*b*. The temperature current flowing across the temperature sensing resistors 14*a* and 14*b* is dependent on the voltage across contact pads 24*d* and 24*e* and the resistances of the temperature sensor elements 14*a* and 14*b*.

The temperature sensing resistors 14*a* and 14*b* act of the voltage divider having a midpoint node coupled to the contact pad 24*f*. If the resistances of the temperature sensing resistors 14*a* and 14*b* are equal to each other (i.e. the fluid temperature is the same as the ambience) than the voltage at the contact pad 24*f* will be exactly half the voltage applied across the contact pads 24*d* and 24*e*. If there is a difference in temperature between the temperature sensing resistors 14*a* and 14*b* then the voltage at the contact pad 24*b* will be higher or lower than the midpoint between the contact pads 24*d* and 24*e* because the resistances of the resistors 14*a* and 14*b* are no longer equal. Because the resistances are no longer equal, but the same current is flowing through both temperature sensing resistors 14*a* and 14*b*, there will be an unequal voltage drop across the temperature sensing resistors 14*a* and 14*b*. Thus, the voltage on the contact pad 24*f* is a differential temperature signal indicative of the temperature difference between the fluid and the ambience.

The thermal connectors 32*a* and 32*b* conduct heat from the fluid to the first temperature sensing resistor 14*a* to ensure that the first temperature sensing resistor 14*a* is the same temperature as the fluid. The thermal connectors 32*a* and 32*b* are positioned on the surface of the fluid test strip 10 in the fluid receiving area 20. The first temperature sensing resistor 14*a* is positioned below the top surface of the fluid test strip 10 under a layer of dielectric material. Thus, in the absence of the thermal connectors 32*a* and 32*b*, the first temperature sensing resistor 14*a* could be thermally isolated from the fluid and could therefore be at a different temperature than the fluid.

The thermal connectors 32*a* and 32*b* are made from a material that is highly thermally conductive. When the fluid is placed on the fluid test strip 10, the thermal connectors 32*a* and 32*b* are in thermal contact with the fluid and quickly arrive at the same temperature as the fluid. The thermal connectors 32*a* and 32*b* are thermally connected to the first temperature sensing resistor 14*a* and they conduct heat to the first temperature sensing resistor 14*a* such that the first temperature sensing resistor 14*a* also arrives very quickly at the same temperature as the fluid. The thermal conductors 32*a* and 32*b* therefore help to ensure that the first and second temperature sensing resistors 14*a* and 14*b* provide an accurate indication of the temperature difference between the fluid and the ambience.

In one example, the electrodes 32*a*-32*c* and contact pads 24*a*-24*f* each have a surface area of about 250 μm. The thermal conductors 32*a* and 32*b* each have a surface area of about 100 μm. The fluid receiving area is for example about 1 mm×2 mm. The length of the electrical connectors 18 is about 1 cm. Thus, the fluid receiving area makes up a relatively small portion of the surface area of the fluid test strip 10. While the great majority of the surface area of the fluid test strip 10 is in the space separating the fluid receiving area from the contact pads 24*a*-24*f*.

In one embodiment the electrodes 30*a*-30*c*, the contact pads 24*a*-24*f*, and the thermal conductors 32*a* and 32*b* are all made of gold. The first and second temperature sensing resistors 14*a* and 14*b* are made of platinum and each a resistance of about 1 kΩ at room temperature.

As described previously in relation to FIG. 1, the fluid test strip can be a blood glucose sensor, a protein sensor, a nucleotide sensor, hormone sensor, or many other types of sensors. The specific materials, dimensions, and physical characteristics such as resistance given above are provided only by way of example. Those of skill in the art will understand that the contact pads 24*a*-24*f*, the electrodes 30*a*-30*c*, and the thermal conductors 32*a* and 32*b* can be made of materials other than gold, for example copper, aluminum, alloys of these metals, or any other suitable conductive materials.

Figure 4A:
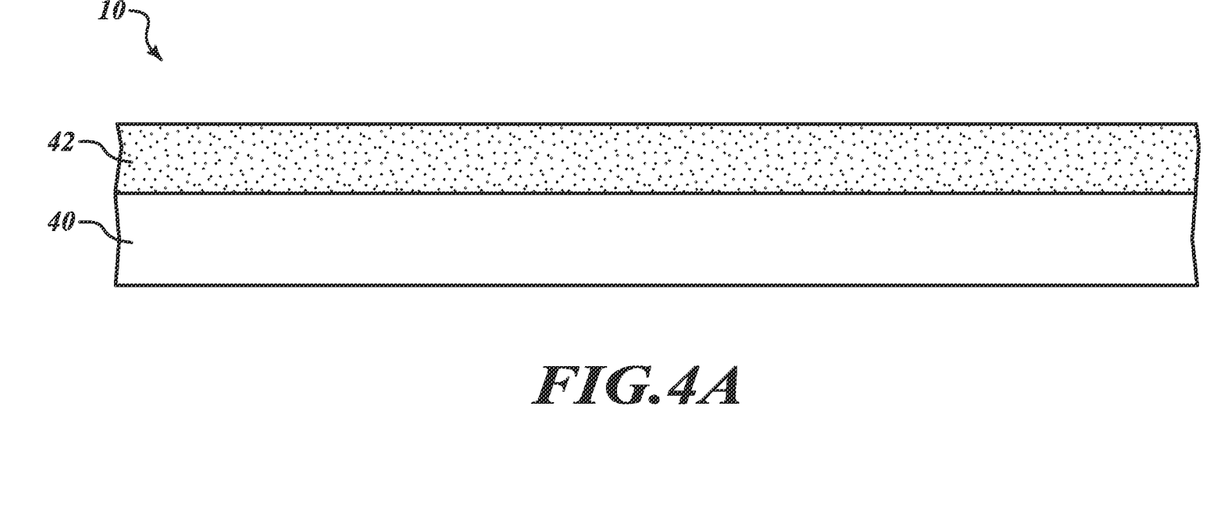
FIGS. 4A-4G are cross-sections of a fluid test strip during successive process steps for forming the fluid test strip according to one embodiment.

FIG. 4A is a cross-section of a fluid test strip 10 at an early stage of manufacture according to one embodiment. Manufacture of the fluid test strip 10 is begun by depositing a first layer of dielectric material 42 on a substrate 40. The first layer of dielectric material 42 is for example a non-photosensitive polyimide 1. The polyimide can be deposited in liquid form on the substrate 40 and spun to achieve a thickness of about 10 μm. After the polyimide has been spun, it is cured so that it hardens on the substrate 40.

The substrate 40 is for example glass and is 750 μm thick. Materials other than polyimide and glass can be used for the first layer of dielectric material 42 and the substrate 40. However it is desirable that the particular materials of the substrate 40 and the first layer of dielectric material 42 are selected such that the substrate 40 can be peeled away from the first layer dielectric material 42 in a subsequent step as only described further below.

Figure 4B:
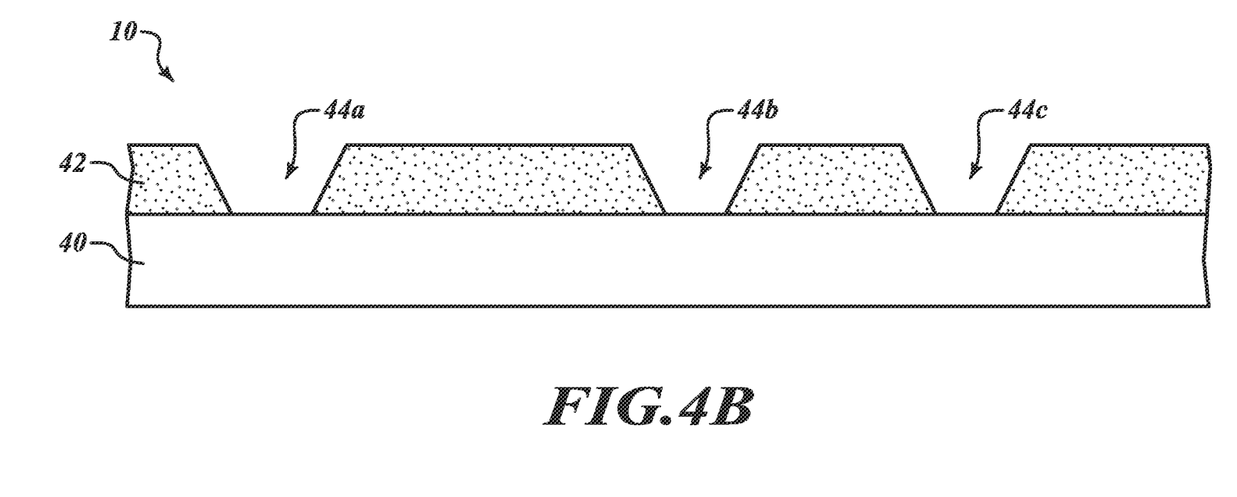

In FIG. 4B, apertures 44a, 44b, and 44c are open in the first layer of dielectric material 42 to expose the substrate 40 below. The apertures 44a, 44b, and 44c are opened by utilizing conventional photolithography steps. For example, photoresist is formed of the first layer of dielectric material 42 and patterned to exposed portions of the first layer of dielectric material 42. An etch step is then performed whereby the exposed portions of the dielectric material 42 are etched leaving apertures 44a, 44b, and 44c in the first layer of dielectric material 42.

Figure 4C:
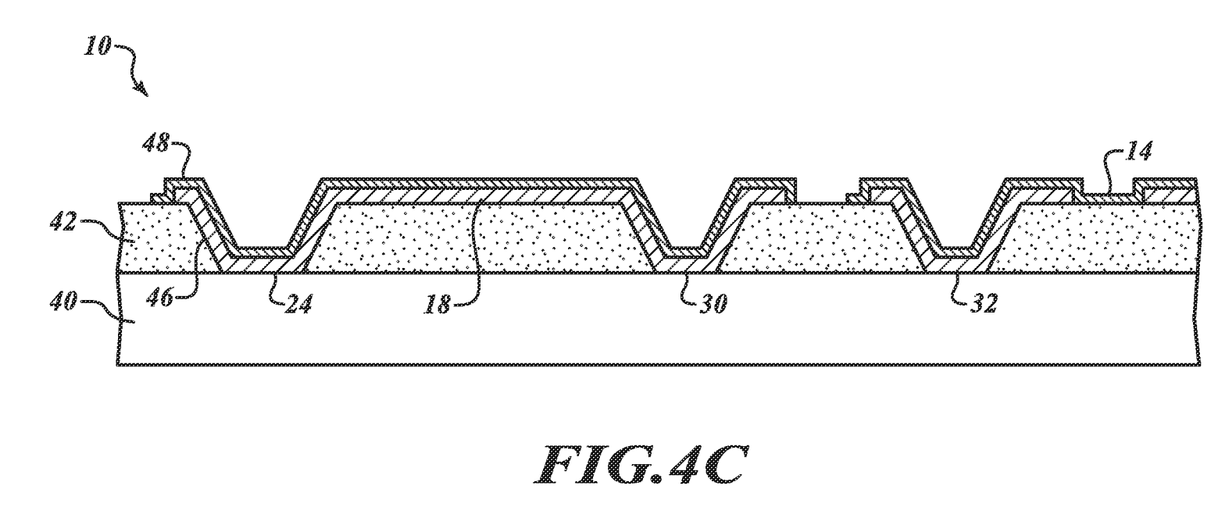

In FIG. 4C, a first layer of conductive material 46 is deposited on the first layer of dielectric material 42 and in the apertures 44a, 44b, and 44c. A portion of the first layer of conductive material 46 is therefore in contact with the substrate 40 in the apertures 44a, 44b, and 44c. The first layer of conductive material 46 is, in one example, gold having a thickness of about 500 nm. The first layer of conductive material 46 can be deposited by physical vapor deposition (PVD), for example by sputtering, to achieve a thin layer with good step coverage in the apertures 44a, 44b, and 44c. The first layer of conductive material 46 is then patterned and etched using conventional photolithography methods as described above. The portions of the first layer of conductive material 46 in the apertures 44a, 44b, and 44c in contact with the substrate 40 correspond to the contact pads 24a-24e, the electrodes 30a-30c, and the thermal conductors 32a-32b of FIG. 2. In FIG. 4C, due to the nature of the cross-section, only one contact pad 24, one electrode 30, and one thermal conductor 32 are shown. The portion 18 of the first layer of conductive material 46 on top of the first layer of dielectric material 42 electrically connecting the contact pad 24 and the electrode 30 corresponds to one of the conductive lines 18 of FIGS. 1-3. The first layer of conductive material 46 can be conductive material other than gold, such as aluminum, copper, or another suitable conductive material with the stipulation that the particular materials of the layer 46 and the substrate 40 be such that the substrate 40 can be peeled away from the contact pad 24, electrode 30, and the thermal conductor 32 without damaging them, as will be explained further below.

A second layer of conductive material 48 is also deposited on the first layer of conductive material 46 and on the first layer of dielectric material 42. In one example the second layer of conductive material 48 is platinum. The second layer of conductive material 48 can be deposited by physical vapor deposition, and has a thickness of about 15 nm. The second layer of conductive material 48 is also patterned and etched using conventional photolithographic methods. In general, the second layer of conductive material 48 remains wherever the first layer of conductive material 46 remains. However the second layer of conductive material 48 forms a temperature sensing resistor 14 of the fluid test strip 10. The portion of the second layer of conductive material 48 that forms the temperature sensing resistor 14 remains on the first layer of dielectric material 42. Though not shown in the cross-section of FIG. 4C, the temperature sensing resistor 14 is electrically coupled to two contact pads by two conductive lines 18.

Not shown in the cross section is a second temperature sensing resistor corresponding to the second temperature sensing resistor 14b of FIG. 3. Despite not being shown in FIG. 4C, the second temperature sensing resistor is also formed of the second conductive material 48 by patterning the first and second conductive materials 46 and 48. In particular the second temperature sensing resistor is formed of the second conductive material 48 positioned in a break between two portions of one of the signal lines 18 not shown in FIG. 4C.

Figure 4D:
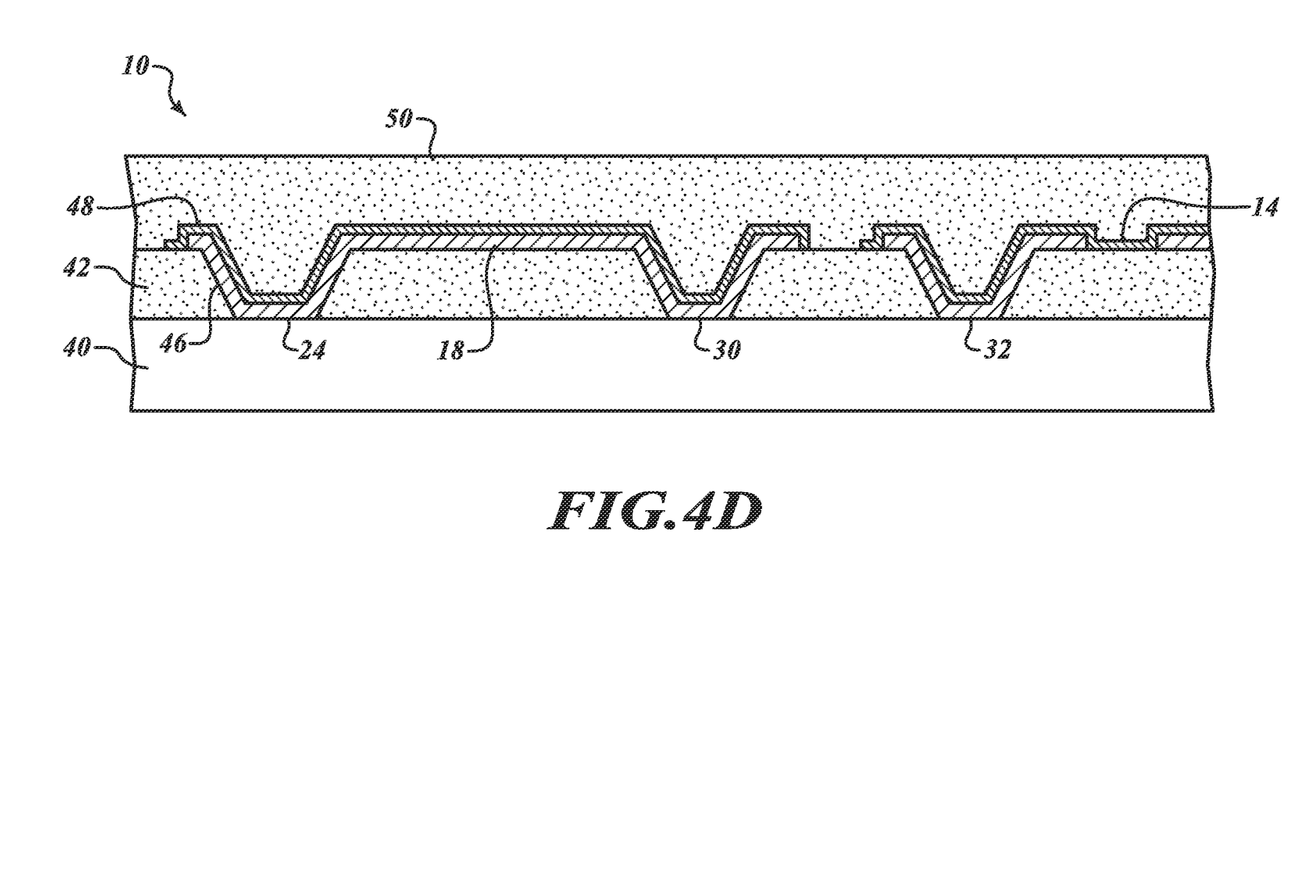

In FIG. 4D a second layer of dielectric material 50 is deposited on the first layer of dielectric material 42 and the second layer of conductive material 48. The second layer of dielectric material 50 is for example polyimide. The second layer of dielectric material 50 can be deposited in liquid form and spun, as described previously, to form a layer about 10 μm thick. The second layer of dielectric material 50 is then hardened by curing.

Figure 4E:
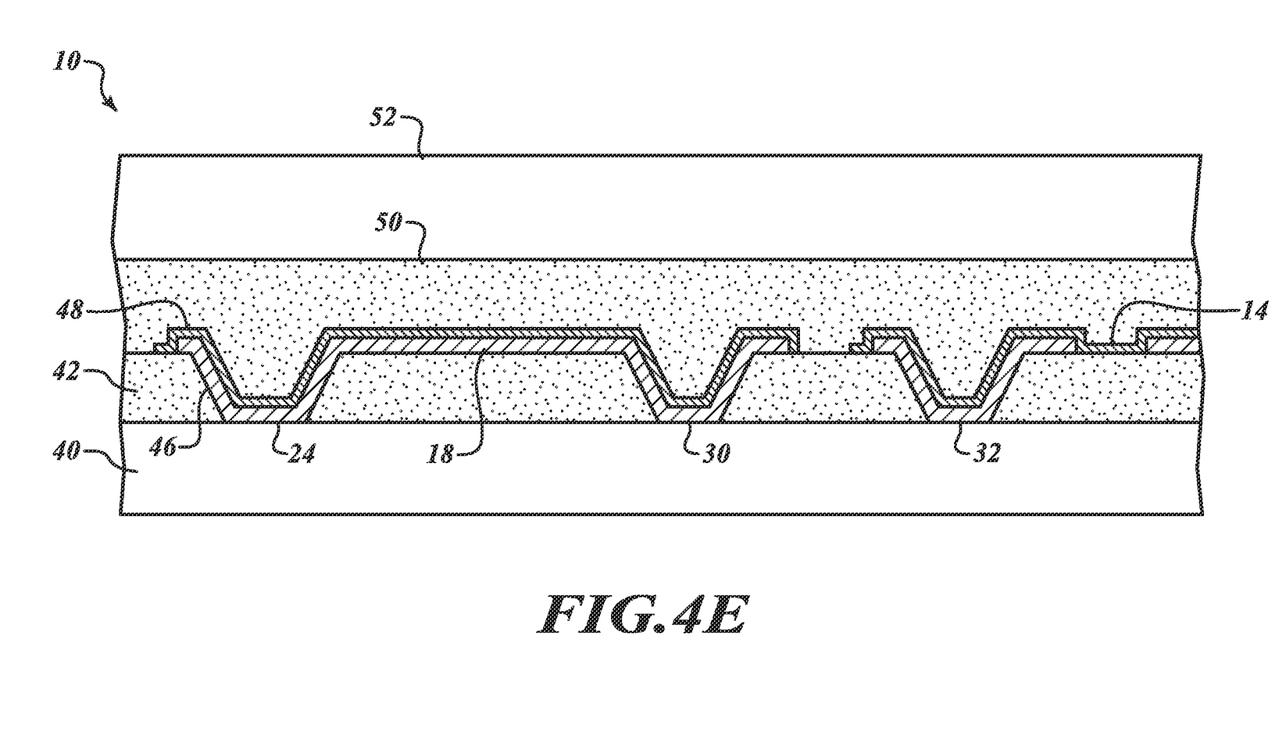

In FIG. 4E an adhesive dielectric layer 52 is deposited on the second layer dielectric material 50. The adhesive dielectric layer 52 is for example a layer of tape which is adhered to the second layer of dielectric material 50. The adhesive dielectric layer 52 is about 150 μm thick and is strongly adhesive to the second layer of dielectric material 52.

Figure 4F:
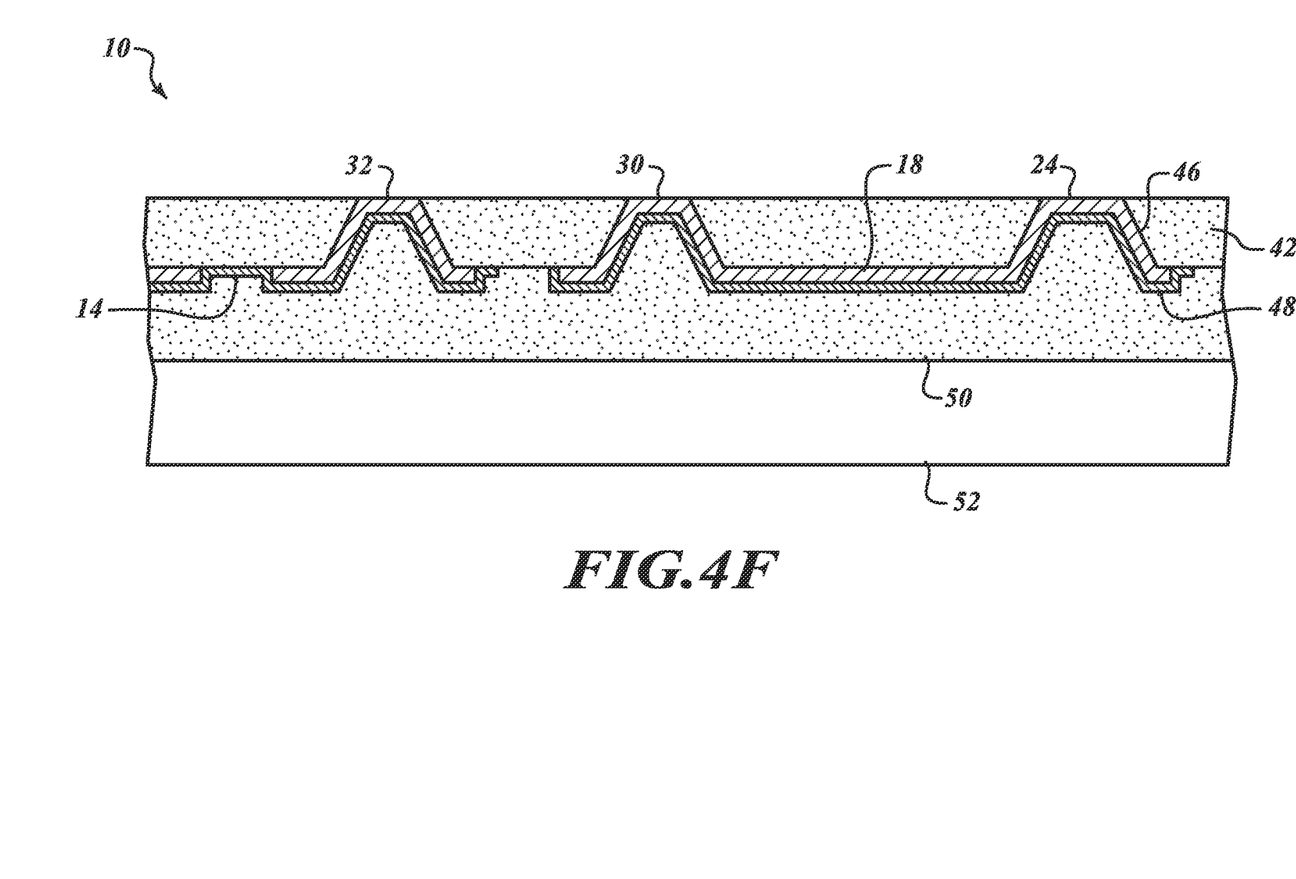

In FIG. 4F, the fluid test strip 10 has flipped over and the substrate 40 has been peeled away. The contact pad 24, the electrode 30, and the thermal conductor 32 are now exposed on the top layer of the fluid test strip 10. The surface of the first layer of dielectric material 42 that was once coupled to the substrate 40 is now the top surface of the fluid test strip 10. Because both the first layer of dielectric material 42 and the first layer of conductive material 46 on the planar surface of the substrate 40, the first layer of dielectric material 42, the contact pad 24, electrode 30, and the thermal conductor 32 share a planar top surface.

Figure 4G:
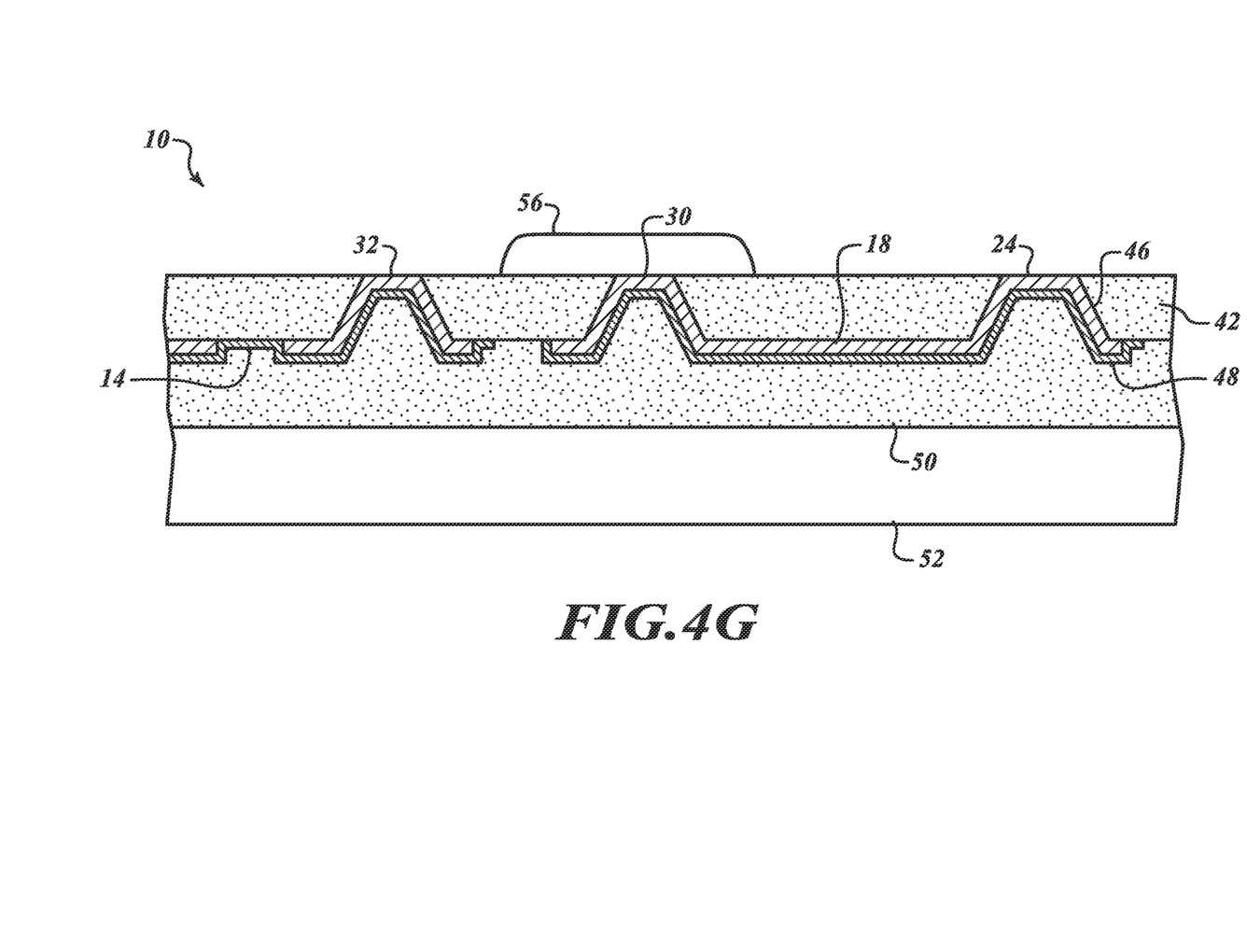

In FIG. 4G an enzyme 56 has been deposited on top of the electrode 30. The particular material of the enzyme 56 depends on the analyte to be detected by the fluid test strip 10. In the example of a blood glucose test strip, the enzyme 56 is glucose oxidase. One blood is placed on the glucose oxidase, a chemical reaction occurs between the glucose oxidase and the glucose in the blood. The chemical reaction releases free electrons into the enzyme 56. This allows a current to flow between electrodes 30b and 30c as described in relation to FIG. 2.

When the fluid is placed on the fluid test strip 10, the fluid covers the enzyme 56 as well as the thermal connector 32. The thermal connector 32 transfers heat from the fluid to the resistor 14. The resistor 14 is then brought the same temperature as that of the fluid as described previously in relation to FIG. 2.

Figure 5:
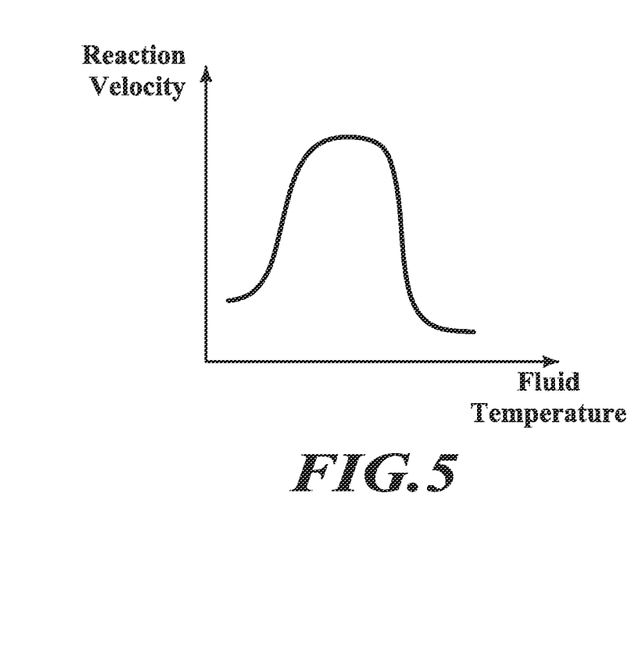
FIG. 5 is a graph of the reaction velocity between the enzyme and the analyte as a function of the temperature of the fluid according to one embodiment.

FIG. 5 is a plot of the reaction velocity between blood glucose and the enzyme glucose oxidase 56 versus temperature. The reaction velocity refers to the velocity of free charges in the enzyme that result from the reaction between glucose and the enzyme. As the reaction velocity increases so does the magnitude of the sensor current. As can be seen, the reaction velocity changes greatly with temperature and not in a linear fashion. By knowing the behavior of the reaction velocity with respect to changes in temperature, the test strip reader 16 can more accurately calculate the concentration of glucose in the blood.

Figure 6:
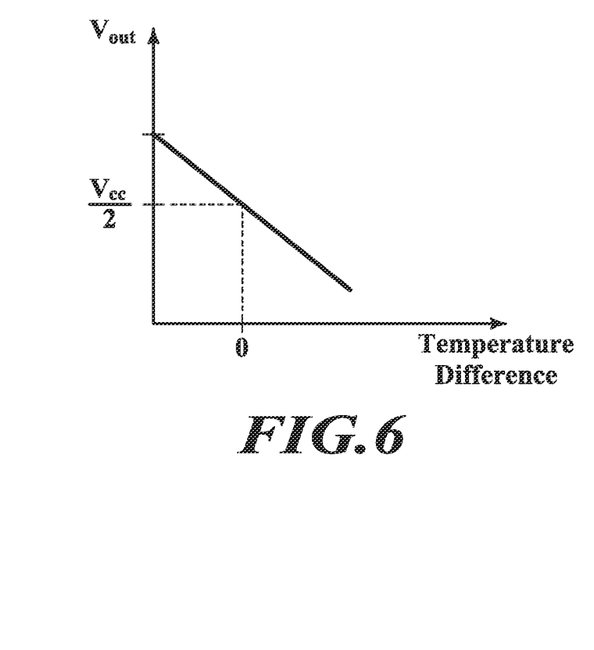
FIG. 6 is a block diagram of a graph of output voltage versus temperature difference between a test fluid and ambience.

FIG. 6 is a plot of the voltage on the contact pad 24F versus the difference in temperature between the first and second temperature sensing resistors 14a and 14b. If a voltage Vcc is applied across the first and second temperature sensing resistors 14a and 14b, then the Vout corresponds to the midpoint voltage between the first and second temperature sensing resistors 14a and 14b. If the resistances of the first and second temperature sensing resistors 14a and 14b are equal, then the temperature difference is 0 Vout is equal to Vcc/2. If the resistance of the second temperature sensing resistor 14b is greater than the resistance of the first temperature sensing resistor 14a, then Vout will be greater than Vcc/2. If the resistance of the second temperature sensing resistor 14b is less than the resistance of the first temperature sensing resistor 14a, then Vout will be less than Vcc/2. The differences in resistance between the first and second temperature sensing resistors 14a and 14b depends on the temperature difference between the first and second temperature sensing resistors 14a and 14b. Whether the resistances of the first and second temperature sensing resistors 14a and 14b increases or decreases with increasing temperature, depends on the TCR of the particular material used to form the temperature sensing resistors 14a and 14b.

Figure 7:
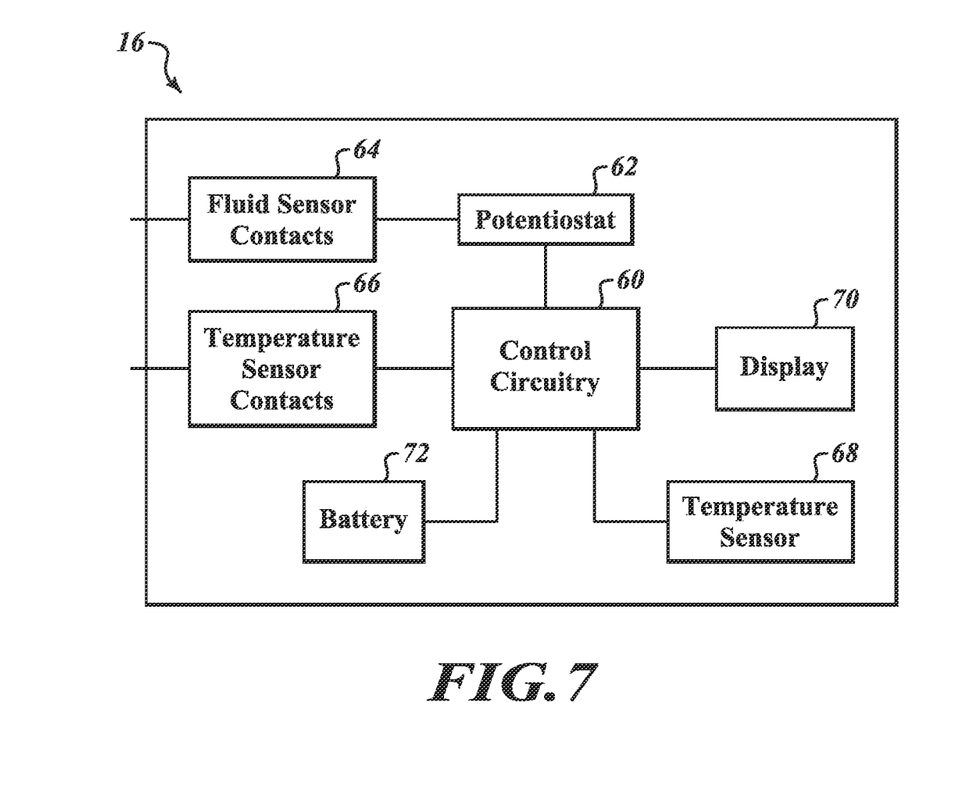
FIG. 7 is a block diagram of a fluid test strip reader according to one embodiment.

FIG. 7 is a block diagram of a fluid test strip reader 16 according to one embodiment. The fluid test strip reader 16 includes control circuitry 60. The control circuitry 60 can include one or more microcontrollers which control the other components of the fluid test strip reader 16 and calculate the concentration of the analyte in the fluid. The control circuitry 60 can also include memory circuits on which are stored tables or databases of values of the concentration of the analyte for various values of temperature difference and sensor current.

A potentiostat 62 is coupled between the control circuitry 60 and fluid sensor contacts 64. The fluid sensor contacts 64 supply voltages to the contact pads 24b and 24c of the fluid test strip 10 as described in relation to FIG. 2. The fluid sensor contacts 64 also receive the sensor current from the contact pads 24b and 24c of the fluid test strip 10. The potentiostat 62 receives the sensor current from the fluid sensor contacts 64 and passes an amplified sensor signal to the control circuitry 60. The control circuitry 60 receives the amplified sensor signal and calculates the value of the concentration of the analyte in the fluid based in part on the amplified sensor signal.

Temperature sensor contacts 66 are also coupled to the control circuitry 60. A voltage is applied between the contact pad 24d and 24e of the fluid test strip 10 via the temperature sensor contacts 66. The temperature difference signal is returned from the temperature sensing resistors 14a and 14b to the temperature sensor contacts 66 via the contact pad 24f of the fluid test strip 10.

The fluid test strip reader 16 also includes a temperature sensor 68. The temperature sensor 68 measures the absolute temperature of the ambience. The control circuitry 60 receives the absolute temperature of the ambience and temperature difference signal and calculates the absolute temperature of the fluid therefrom. The control circuitry 60 calculates the concentration of the analyte in the fluid based on both the absolute temperature of the fluid and the sensor signal as described previously with relation to FIG. 2.

The fluid test strip reader 16 further includes a display 70 coupled to the control circuitry 60. The control circuitry 60 outputs on the display 70 the calculated value of the concentration of the analyte in the fluid. The display allows a technician to view the calculated concentration of the analyte. The fluid test strip reader 16 is powered by battery 72 coupled to the control circuitry 60.

Figure 8:
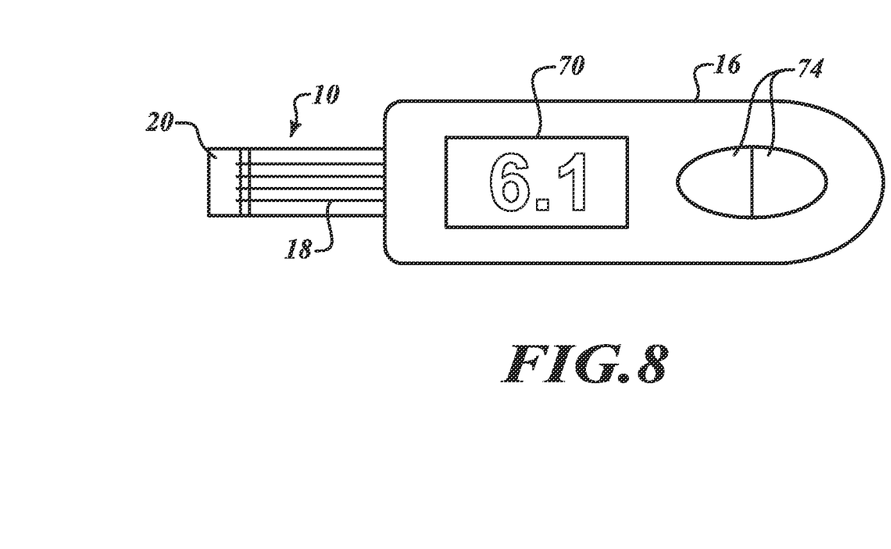
FIG. 8 is an illustration of a fluid test strip coupled to a fluid test strip reader according to one embodiment.

FIG. 8 is an illustration of fluid test strip reader 16 having a fluid test strip 10 coupled thereto. The fluid receiving area 20 is visible on the left side of the fluid test strip 10. The electrodes and thermal conductors are not shown. The electrical connectors 18 connect the components in the fluid receiving area to contact pads 24a-24e which are coupled within the fluid test strip reader 16 and are not visible in FIG. 8D. When the fluid test strip 10 is coupled to the fluid test strip reader 16 and fluid is placed in the fluid receiving area 20, a technician can operate buttons 74 of the fluid test strip reader 16 to initiate a measurement of the concentration of the analyte in the fluid. The fluid test strip reader 16 calculates the value of the concentration of the analyte based on both the temperature and the sensor signals as described previously. The value of the concentration of the analyte in the fluid is then displayed on the display 70.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A fluid test strip comprising:
a fluid receiving area configured to receive a fluid to be tested;
a first electrode positioned in the fluid receiving area;
a second electrode positioned in the fluid receiving area;
an enzyme covering the first and second electrodes;
a first contact pad electrically coupled to the first electrode;
a second contact pad electrically coupled to the second electrode; and
a first resistor positioned within the fluid receiving area and configured to output a temperature signal indicative of a temperature of the fluid to be tested; and
a dielectric material between the first resistor and the enzyme.

2. The fluid test strip of claim 1, further comprising a second resistor electrically coupled to the first resistor at a node.

3. The fluid test strip of claim 2 wherein the temperature signal is a differential temperature signal indicative of a temperature difference between the first and the second resistors.

4. The fluid test strip of claim 3 wherein the further comprising a third contact pad electrically coupled to the first resistor.

5. The fluid test strip of claim 4 wherein the third contact pad is electrically coupled to the node.

6. The fluid test strip of claim 1 wherein the first contact pad is configured to supply a first voltage to the first electrode.

7. The fluid test strip of claim 6 wherein the second contact pad is configured to supply an output signal indicative of a concentration of a compound in the fluid to be tested.

8. The fluid test strip of claim 7 wherein the output signal is a current passing between the first and the second electrodes.

9. A device for measuring a concentration of a compound in a fluid, the device comprising:
a substrate;
a first electrode overlying the substrate;
a second electrode overlying the substrate;
a first resistor overlying the substrate;
an enzyme overlying the first electrode, the second electrode, and the first resistor, the enzyme configured to react with the compound when the fluid contacts the enzyme;
a dielectric material between the first resistor and the enzyme;
a first contact pad on the substrate, the first contact pad being configured to supply a first voltage to the first electrode;
a second contact pad on the substrate, the second contact pad being electrically coupled to the second electrode, the second contact pad configured to output a compound concentration signal indicative of the concentration of the compound in the fluid; and
a third contact pad coupled to the first resistor and configured to output a temperature signal indicative of a temperature of the fluid.

10. The device of claim 9, further comprising a thermal connector on the substrate, the thermal connector configured to couple the first resistor to the fluid.

11. The device of claim 9 comprising:
a second resistor on the substrate, the second resistor being electrically coupled to the first resistor and the third contact pad, the second resistor being positioned outside an area of the device covered by the enzyme;
a fourth contact pad on the substrate, the fourth contact pad being electrically coupled to the second resistor; and
a fifth contact pad on the substrate, the fifth contact pad being electrically coupled to the first resistor.

12. The device of claim 11 wherein the fourth contact pad is configured to supply a second voltage to the first resistor, the fifth contact pad being configured to supply a third voltage to the second resistor, the third contact pad being electrically coupled between the first and the second resistors, the output temperature signal having a voltage between the first and second voltages and indicative of a temperature difference between the first and second resistors.

13. The device of claim 12 wherein the substrate and the contact pads are configured to interface with a compound concentration sensor configured to supply the first, second, and third voltages to the first, fourth, and fifth contact pads, and to receive the compound concentration signal and the output temperature signal from the second and third contact pads, respectively.

14. A system comprising:
a fluid test strip including:
a fluid receiving area configured to receive a fluid;
a test electrode in the fluid receiving area configured to provide an output signal indicative of a concentration of a compound in the fluid;
a dry area spaced apart from the fluid receiving area;
a first contact pad in the dry area electrically coupled to the test electrode;
a first temperature sensor having a first portion in the dry area and a second portion in the fluid receiving area;
a dielectric material between the first portion and the fluid; and
a second contact pad in the dry area and electrically coupled to the first temperature sensor, the first temperature sensor being configured to output a first temperature signal indicative of a difference in a temperature of the fluid and a temperature of the dry area;
a fluid test strip reader including:
a port configured to receive the fluid test strip; and
control circuitry configured to supply power to the fluid test strip, to receive the first temperature signal and the output signal from the fluid test strip, and to calculate a value of the concentration of the compound in the fluid based on the first temperature signal and the output signal.

15. The system of claim 14 wherein the fluid test strip reader includes a second temperature sensor configured to provide a second temperature signal to the control circuitry.

16. The system of claim 15 wherein the control circuitry calculates the value of the concentration of the compound based in part on the second temperature signal.

17. The system of claim 16 wherein the second temperature signal is indicative of an ambient temperature.

18. The system of claim 17 wherein the control circuitry calculates a temperature of the fluid based on the first and the second temperature signals.

19. A biosensor, comprising:
a fluid receiving area, including
a fluid sensor having a plurality of fluid sensor electrodes;
an enzyme covering the fluid sensor electrodes;
a fluid temperature sensor element; and
a dielectric material between the enzyme and the fluid temperature sensor element; and
a dry area, spaced apart from the fluid receiving area, the dry area including
an ambient temperature sensor element; and
a plurality of contact pads, each contact pad coupled to one of the fluid sensor electrodes or to the temperature sensor element.

20. The biosensor of claim 19, further comprising a thermal connector in thermal communication with the fluid temperature sensor element, the thermal connector having a surface area that is substantially larger than a surface area of the fluid temperature sensor element.

21. The biosensor of claim 19 wherein the ambient temperature sensor element is coupled in parallel with the fluid temperature sensor element to provide a differential temperature measurement of the fluid relative to an ambient temperature.

* * * * *